United States Patent [19]
Sanpietro

[11] Patent Number: 5,562,626
[45] Date of Patent: Oct. 8, 1996

[54] SAFETY SYRINGE

[76] Inventor: Joseph A. Sanpietro, 212 Stillhouse Rd., Freehold, N.J. 07728

[21] Appl. No.: 526,166

[22] Filed: Sep. 11, 1995

[51] Int. Cl.$^6$ ................................................ A61M 5/00
[52] U.S. Cl. ................................. 604/110; 604/263
[58] Field of Search .................................. 604/110, 187, 604/198, 263, 195, 136, 192

[56] References Cited

U.S. PATENT DOCUMENTS

| | | | |
|---|---|---|---|
| 5,282,793 | 2/1994 | Larson | 604/198 X |
| 5,318,538 | 6/1994 | Martin | 604/110 |
| 5,367,080 | 12/1994 | Petrussa. | |
| 5,411,487 | 5/1995 | Castagna | 604/198 |
| 5,417,660 | 5/1995 | Martin | 604/198 X |
| 5,433,712 | 7/1995 | Stiles et al. | 604/110 X |

*Primary Examiner*—John D. Yasko
*Attorney, Agent, or Firm*—Plevy & Associates

[57] ABSTRACT

A safety syringe having a sheath that automatically extends over the needle of the syringe after the syringe is used to administer an injection. The safety sheath that extends over the needle of the syringe is stored in a retracted position around the exterior of the syringe barrel. Locking pawls extend from the sheath and engage the syringe barrel thereby retaining the sheath in the retracted position. A spring element is disposed between the syringe barrel and the sheath, wherein the spring is compressed when the sheath is in its retracted position. As an injection is made and a plunger assembly is advanced within the syringe barrel, a trigger flange on the plunger assembly displaces the locking pawls, thereby releasing the lock between the syringe barrel and the sheath. With the release of the locking means that retains the sheath, the bias of the compressed spring moves the sheath forward on the syringe barrel. The sheath comes to rest at an orientation where the sheath extends beyond the needle of the syringe, thereby protecting the needle from accidental contact. A second locking mechanism then locks the sheath into the extended position, preventing the syringe from being reused.

10 Claims, 4 Drawing Sheets

SAFETY SYRINGE

BACKGROUND OF THE INVENTION

1. Field of the Invention

The present invention relates to hypodermic syringes with a safety sheath, wherein the safety sheath automatically extends over the needle of the syringe after the syringe has been used.

2. Description of Prior Art

It is well known that many serious diseases, such as Acquired Immune Deficiency Syndrome and Hepatitis can be spread or transmitted by blood or other bodily fluids. It is a major concern to health care workers who administer medications using hypodermic needles, that the needles may accidentally stick or prick the health care worker transmitting a disease from a patient to the health care worker. This can happen, for example, when the patient pulls back suddenly upon insertion or removal of the needle, or when the needle is being handled for disposal.

In order to prevent such accidental needle sticks or pricks, many inventions have been made which provide a protective sheath that covers the needle. In some cases, the sheath has to be manually removed or replaced over the needle. Such safety syringes are problematic, because it is very easy to stab or stick oneself in the hand trying to remove or replace the sheath. In other cases, the sheath is slidably mounted on the syringe to uncover and cover the needle. Bias means are often employed to urge the sheath into the extended or covering position. While this is an improvement over a manually removable sheath, in many cases, some type of locking or latching mechanism is employed to retain the sheath either in the retracted or extended position. Such a locking mechanism again must be manually actuated with the hand or fingers, exposing the hand to accidental pricks while manipulating the mechanism.

Some safety syringes have protective sheaths that do automatically extend after the syringe is used, thereby preventing the need to manually engage a locking mechanism. In such syringes, the extending sheath is triggered by the advancement of plunger into the syringe barrel. Such prior art safety syringes are exemplified by U.S. Pat. No. 5,376,080 to Petrussa, entitled SINGLE USE RETRACTABLE NEEDLE SYRINGE. The problems associated with such prior art safety syringes is that since the sheath extending mechanism is triggered by the use of the syringe and not by direct manipulation, the sheath extending mechanism tends to be of a complex design. This makes such safety syringes both difficult and expensive to manufacture.

It is therefore and objective of the present invention to provide a safety syringe with a safety sheath that automatically extends over the needle of the syringe after the syringe is used.

It is a further objective of the present invention to provide a safety syringe with an automatically extending sheath that is low cost, easy to manufacture and simple to operate.

SUMMARY OF THE INVENTION

The present invention is a safety syringe wherein a sheath automatically extends over the needle of the syringe after the syringe is used to administer an injection. The safety sheath that extends over the needle of the syringe is stored in a retracted position around the exterior of the syringe barrel. Locking pawls extend from the sheath and engage the syringe barrel, thereby retaining the sheath in the retracted position. A spring element is disposed between the syringe barrel and the sheath, wherein the spring is compressed when the sheath is in its retracted position. As an injection is made and a plunger assembly is advanced within the syringe barrel, a trigger flange on the plunger assembly displaces the locking pawls, thereby releasing the lock between the syringe barrel and the sheath. With the release of the locking means that retains the sheath, the bias of the compressed spring moves the sheath forward on the syringe barrel. The sheath comes to rest at an orientation where the sheath extends beyond the needle of the syringe, thereby protecting the needle from accidental contact. A second locking mechanism then locks the sheath into the extended position, preventing the syringe from being reused.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE PRESENT INVENTION

Figure 1:
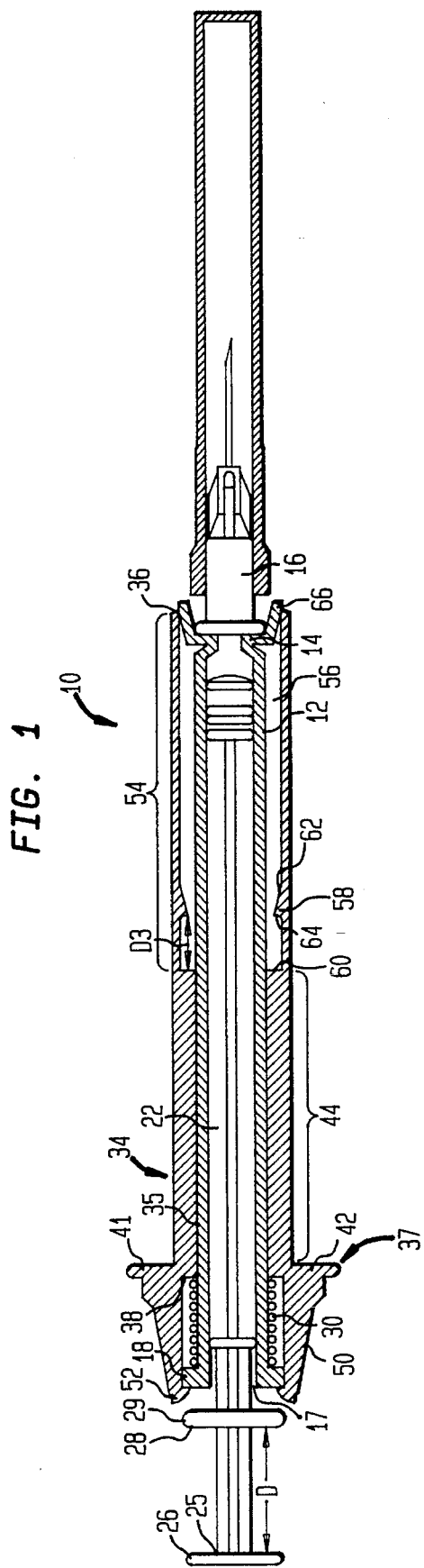
FIG. 1 is a cross-sectional view of one preferred embodiment of the present invention safety syringe, shown in an unused condition.
Figure 2:
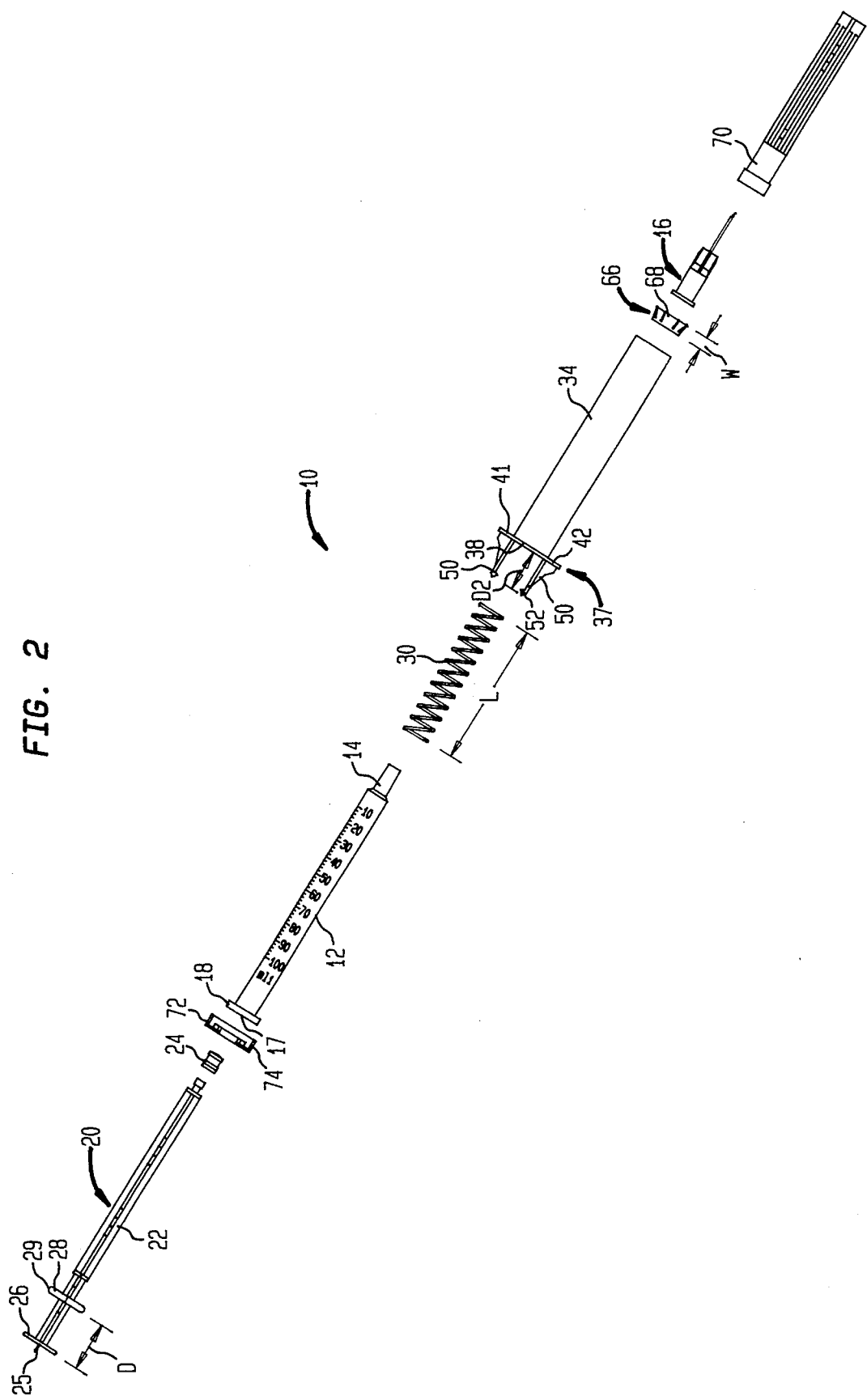
FIG. 2 is an exploded side view of the present invention safety syringe.

Referring to FIG. 1 in conjunction with FIG. 2, a preferred embodiment of the present invention safety syringe 10 is shown. The safety syringe 10 includes a conventional syringe barrel 12 such as that found ordinary hypodermic syringes. The syringe barrel 12 can be any size, depending upon the intended use of the safety syringe 10 and the volume of solution to be injected or drained. The syringe barrel 12 has a tapered neck region 14 adapted to receive a conventional needle hub assembly 16. Needle hub assemblies that attach to syringe barrels with adhesive, a threaded coupling or a bayonet coupling are well known in the art. Any such needle hub assembly interconnection can be used in conjunction with the present invention. The syringe barrel 12 has an open bottom end 17 opposite the tapered neck region 14. The open bottom end 17 receives the plunger assembly 20, whereby the plunger assembly 20 extends through the open bottom end 17 of the syringe barrel 12. A circular flange 18 radially extends from the syringe barrel 12 proximate the open bottom end 17.

The plunger assembly 20 includes a plunger shaft 22 and an elastomeric grommet 24 that joins to the top of the plunger-shaft 22 in typical prior art fashion. The elastomeric grommet 24 creates a seal with the interior of the syringe barrel 12 when the plunger assembly 20 is advanced within the syringe barrel 12. As such, by reciprocally moving the plunger assembly 20 within the syringe barrel 12, liquid can be displaced from, or drawn into, the syringe barrel 12 through the needle hub assembly 16. The bottom end 25 of the plunger shaft 22 terminates in a push flange 26, as is typical of most all syringe plunger shafts. However, a trigger flange 28 radially extends from the plunger shaft 22 a predetermined distance D from the bottom end 25. The trigger flange 28 is rigid, having a rounded peripheral edge 29.

A spring element 30 passes over the exterior of the syringe barrel 12. The spring element 30 has an uncompressed length L (FIG. 2) and a diameter that enables the spring element 30 to be positioned around the syringe barrel 12, wherein the spring element 30 abut against the circular flange 18 at the bottom end 17 of the syringe barrel 12.

The safety sheath 34 is a tubular structure having an open top end 36 and an open bottom end 38. A finger flange 37 extends outwardly from the exterior of the sheath 34, immediately proximate the open bottom end 38. The finger flange 37 provides at least two contact surfaces 41, 42 upon which two fingers of a hand may rest when using the safety syringe 10. From FIG. 1, it can be seen that the hollow structure of the sheath 34 does not define a uniform channel between the open end 36 and the open bottom end 38. Rather, in a first region 44 of the sheath 34, the channel 35 defined by the sheath 34 is only slightly larger than the outside diameter of the syringe barrel 12. As a result, the syringe barrel 12 may freely pass through the first region 44 of the sheath 34, but the spring element 30 surrounding the syringe barrel 12 can not. As a result, when the syringe barrel 12 is advanced through the first region 44 of the sheath 34, the spring element 30 becomes compressed between the bottom end 38 of the sheath 34 and the circular flange 18 at the bottom of the syringe barrel 12.

Two pawls 50 extend downwardly from the finger flange 37 at the bottom of the safety sheath 34. The pawls 50 are parallel, but are flexible and can be elastically spread apart. Each pawl 50 extends a distance D2 (FIG. 2) from the bottom of the sheath 34. The distance D2 is at least as great as the length of spring element 30 when fully compressed. Each pawl 50 terminates at a hook projection 52 that faces the opposite pawl. As the syringe barrel 12 is advanced into the sheath 34, the spring element 30 compresses, thereby resisting the advancement of the syringe barrel 12. The syringe barrel 12 is advanced into the sheath 34 against the bias of the spring element 30 until the hook projections 52 on the tip of each pawl 50 engage the circular flange 18 at the bottom of the syringe barrel 12. The pawls 50 retain the syringe barrel 18 in place against the bias of the spring element 30 until the safety syringe 10 is triggered during use, as will later be explained.

In FIG. 1, it can be seen that the second region 54 in the upper portion of the sheath 34 defines a larger channel 56 than does the lower first region 44. The channel 56 in the second region 54 is generally uniform, having the same general diameter as does the open top end 36 of the sheath 34. A locking protrusion 58 extends inwardly in the second region 54. The locking protrusion 58 is disposed a predetermined distance D3 from the transition point 60 between the first region 44 and second region 54 within the sheath 34. The locking protrusion 58 has a tapered surface 62 facing the open top end 36 of the sheath 34 and a flat surface 64 facing the open bottom end of the sheath 34.

Referring to both FIG. 1 and FIG. 2, an expansion collar 66 is shown. The expansion collar 66 has a width W that is no wider than the predetermined distance D3 between the locking protrusion 58 and transition point 60 (FIG. 1). The expansion collar 66 fits over the tapered neck region 14 of the syringe barrel 12 and is retained on the syringe barrel 12 by the coupling of the needle hub assembly 16 to the syringe barrel 12. The expansion collar 66 has a plurality of locking tabs 68 that are angled toward the needle hub assembly 16.

The locking tabs 68 are hinged to the expansion collar 66 and are capable of flaring outwardly away from the expansion collar 66 when biased away from the needle hub assembly 16.

Figure 3:
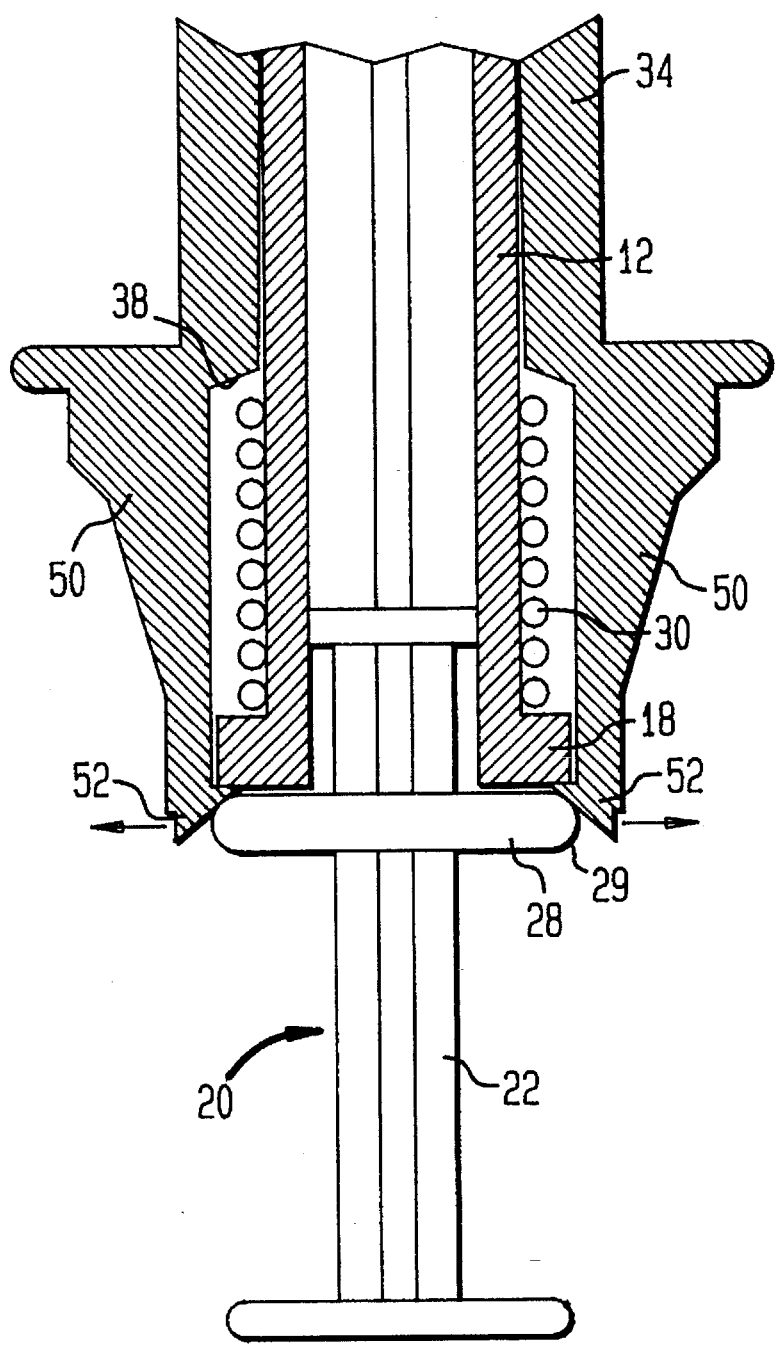
FIG. 3 is an enlarged cross-sectional view of a segment of the present invention safety syringe, used to better illustrate the trigger mechanism contained within the present invention.

To use the present invention safety syringe 10, medicine or the like is drawn into the syringe barrel 12 through the needle hub assembly 16 in the traditional manner. Once full, an injection is also made in a traditional manner, wherein the needle is advanced into a patient and the plunger assembly 20 is advanced within the syringe barrel 12 to displace the medicine through the needle hub assembly 16. Referring to FIG. 3, it can be seen that as the plunger assembly 20 is advanced into the syringe barrel 12, the spring element 30 compresses and the trigger flange 28 on the plunger shaft 22 eventually contacts the pawls 50 that extend below the sheath 34. As the trigger flange 28 is pressed against the pawls 50, the rounded peripheral edge 29 of the trigger flange 28 abuts against the hooks projections 52, thereby forcing the pawls 50 to spread apart from one another. As the pawls 50 spread, they are forced to a point where they no longer engage the circular flange 18 at the bottom of the syringe barrel 12. As the trigger flange 28 is further advanced, it fully spreads the pawls 50 and the trigger flange 28 abuts against the circular flange 18 at the bottom of the syringe barrel 12. As the advancing force on the plunger assembly 20 is removed, the force from the spring element 30 moves the circular flange 18 back down past the pawls 50. The abutment of the trigger flange 28 against the circular flange 18 prevents the pawls 50 from reengaging the circular flange 18 and the open bottom end 38 of the sheath 34 is forced away from the circular flange 18 at the syringe barrel 12.

Figure 4:
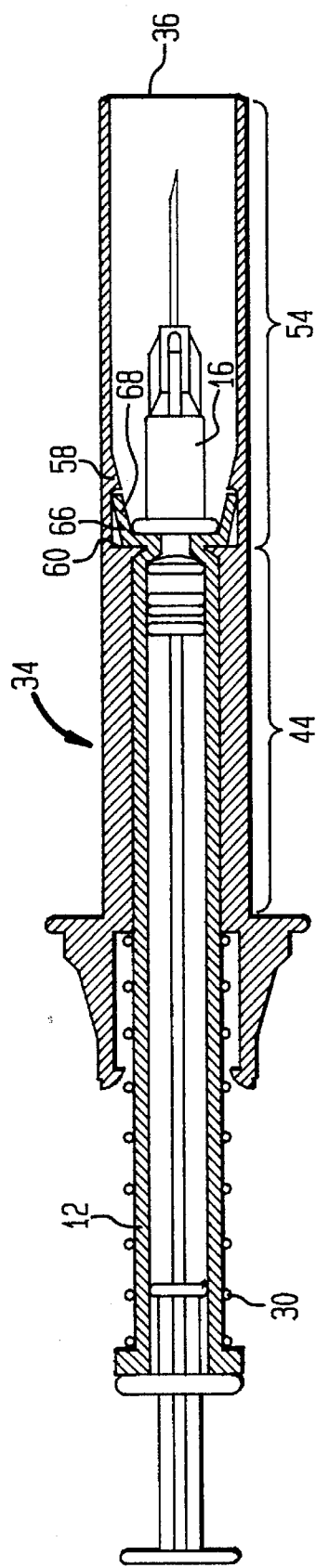
FIG. 4 is a cross-sectional view of the present invention safety syringe, shown in a used condition.

Referring to FIG. 4, it can be seen that as the spring element 30 moves the bottom of the syringe barrel 12 away from the bottom of the sheath 34, the needle hub assembly 16 and expansion collar 66 are retracted into the second region 54 of the sheath 34. The retraction of the needle hub assembly 16 is stopped when the expansion collar 66 abuts against the transition point 60 between the first region 44 and second region 54 within the sheath 34. At this point, the expansion collar 66 has been drawn past the locking protrusion 58. The locking protrusion 58 engages the locking tabs 68 on the expansion collar 66, preventing the syringe barrel 12 from again being manually advanced into the sheath 34. As a result, the engagement of the expansion collar 66 with the locking protrusion 58 prevents the safety syringe 10 from being reused after the sheath 34 has been extended over the needle hub assembly 16.

Once the spring element 30 is triggered, the open top end 36 of the safety sheath 34 extends beyond the tip of the needle on the needle hub assembly 16. As such, the needle is shielded from accidental contact. Furthermore, the advancement of the sheath 34 over the needle hub assembly 16 begins at the instant the injection is complete and the plunger assembly 20 is fully advanced into the syringe barrel 12. As a result, the safety sheath 34 extends over the needle hub assembly as the needle is removed from the patient, thereby protecting the tip of the needle during extraction even if the patient were to move suddenly.

Returning to FIG. 2, two prior use safety mechanisms are also used in conjunction with the present invention safety syringe 10. First, a removable needle cap 70 is used to protect the unused needle. The needle cap 70 engages the needle hub assembly 16 with an interference fit. A trigger guard 72 is also provided. The trigger guard 72 engages the plunger shaft 22, and contains a side wall structure 74 that passes around the exterior of the pawls 50. The presence of the trigger guard 72 prevents the trigger flange 28 from engaging the pawls 50 and also prevents the pawls 50 from spreading. As a result, the trigger guard 72 prevents the activation of the mechanism that advances the safety sheath 34 over the needle hub assembly 16. Both the needle cap 70 and the trigger guard 72 are removed from the safety syringe 10 prior to its use.

It will be understood that the embodiment described herein is merely exemplary and that a person skilled in the art of syringe design may make numerous alternate embodiments, variations and modifications without departing from the spirit and scope of the invention. All such variations and modifications are intended to be included within the scope of the invention as defined by the appended claims.

What is claimed is:

1. A hypodermic syringe device, comprising:
   a syringe barrel having a first end and a second end, said syringe barrel having a flange radially extending from said second end;
   a needle hub assembly coupled to said first end of said syringe barrel;
   a plunger extending into said syringe barrel through said second end of said syringe barrel, said plunger being reciprocally positionable within said barrel between an advanced position and a retracted position;
   a sheath having a first end and a second end, wherein said syringe barrel extends into said first end of said sheath, said syringe barrel being reciprocally positionable within said sheath between an unused position and a used position;
   spring bias means for biasing said syringe barrel toward said used position relative said sheath;
   locking means affixed to said first end of said sheath for engaging said flange on said second end of said syringe barrel and retaining said syringe barrel at said unused position, said locking means automatically disengaging said syringe barrel when said plunger is moved to said advanced position, wherein said spring bias means moves said syringe barrel to said used position within said sheath.

2. The device according to claim 1, wherein said needle hub assembly is disposed within said sheath when said syringe barrel is at said used position.

3. The device according to claim 1, further includes a means for automatically locking said syringe barrel in place when said syringe barrel moves to said used position within said sheath, thereby preventing said syringe barrel from being moved out of said used position.

4. The device according to claim 1, wherein said spring bias means is a coil spring disposed around said syringe barrel, said coil spring being compressed between said flange and said sheath when said syringe barrel is at said unused position.

5. The device according to said claim 1, wherein said locking means includes at least one pawl that engages and retains said flange when said syringe barrel is at said unused position.

6. The device according to claim 5, wherein said plunger has an element thereon that contacts said at least one pawl and disengages said at least one pawl from said flange when said plunger is moved to said advanced position within said syringe barrel.

7. The device according to claim 1, further including an expansion collar coupled to said first end of said syringe barrel, said expansion collar engaging said sheath when said syringe barrel is at said used position in said sheath, wherein said expansion collar prevents said syringe barrel from moving away from said used position in said sheath.

8. The device according to claim 1, further including a guard member removably coupled to said plunger, wherein said guard member prevents said plunger from extending into said syringe barrel to said advanced position.

9. The device according to claim 6, wherein said at least one panel consists of two pawls, wherein each of said pawls are unistructurally formed as part of said sheath.

10. A hypodermic syringe device, comprising:
    a syringe barrel having a first end and a second end;
    a needle hub assembly coupled to said first end of said syringe barrel;
    a plunger extending into said syringe barrel through said second end of said syringe barrel, said plunger being reciprocally positionable within said barrel between an advanced position and a retracted position;
    a sheath having a first end and a second end, wherein said syringe barrel extends into said first end of said sheath, said syringe barrel being reciprocally positionable within said sheath between an unused position and a used position;
    spring bias means for biasing said syringe barrel toward said used position relative said sheath;
    locking means affixed to said first end of said sheath, for engaging said syringe barrel and retaining said syringe barrel at said unused position, said locking means automatically disengaging said syringe barrel when said plunger is moved to said advanced position, wherein said spring bias means moves said syringe barrel to said used position within said sheath; and
    an expansion collar coupled to said first end of said syringe barrel, said expansion collar engaging said sheath when said syringe barrel is at said used position in said sheath, wherein said expansion collar prevents said syringe barrel from moving away from said used position in said sheath.

* * * * *